United States Patent
Cullup

(10) Patent No.: US 8,033,287 B2
(45) Date of Patent: Oct. 11, 2011

(54) DISPOSABLE, BIODEGRADABLE, PORTABLE DENTAL IMPLEMENT

(76) Inventor: Martin Cullup, Bow, WA (US)

(*) Notice: Subject to any disclaimer, the term of this patent is extended or adjusted under 35 U.S.C. 154(b) by 796 days.

(21) Appl. No.: 12/008,380

(22) Filed: Jan. 9, 2008

(65) Prior Publication Data
US 2009/0172902 A1 Jul. 9, 2009

(51) Int. Cl.
A45D 44/18 (2006.01)

(52) U.S. Cl. ........................ 132/309; 132/329

(58) Field of Classification Search .......... 132/308–310, 132/321–329, 312–313; 206/362.4, 383, 206/382, 63.5, 368, 369–370
See application file for complete search history.

(56) References Cited

U.S. PATENT DOCUMENTS

| | | | |
|---|---|---|---|
| 1,149,376 A | 8/1915 | Leonard | |
| 3,070,102 A | 12/1962 | MacDonald | |
| 3,298,507 A | 1/1967 | Micciche | |
| 3,438,486 A * | 4/1969 | Pinkas | 206/104 |
| 3,943,592 A | 3/1976 | Bhaskar et al. | 15/160 |
| 3,952,867 A | 4/1976 | McCord | 206/229 |
| 4,998,978 A | 3/1991 | Varum | 132/321 |
| 5,735,300 A * | 4/1998 | Higgins | 132/329 |
| 6,085,761 A * | 7/2000 | Inaba | 132/329 |
| 6,921,409 B2 | 7/2005 | Richard | 606/161 |
| 7,798,156 B2 * | 9/2010 | Kelly | 132/308 |

* cited by examiner

Primary Examiner — Todd Manahan
Assistant Examiner — Brianne O'Neill
(74) Attorney, Agent, or Firm — Dean A. Craine

(57) ABSTRACT

A multiple, disposable, biodegradable dental implement system in which a plurality of disposable, flat dental implements are formed from a large planar blank. Each dental implement includes a flat toothbrush head and a flat gum massager head formed on opposite ends of a flat elongated shank. Adjacent implements are formed in the blank by perforation lines that allow the implements to be individually detached from the blank just prior to use. In the preferred embodiment, each toothbrush head includes a plurality of concave ridges formed while the gum massaging head is made of a plurality of convex curved ridges complimentary with the concave ridges on the adjacent toothbrush. The planar blank is made of disposable paper and embedded with dry toothpaste or mouthwash which is activated by the user's saliva when used.

7 Claims, 1 Drawing Sheet

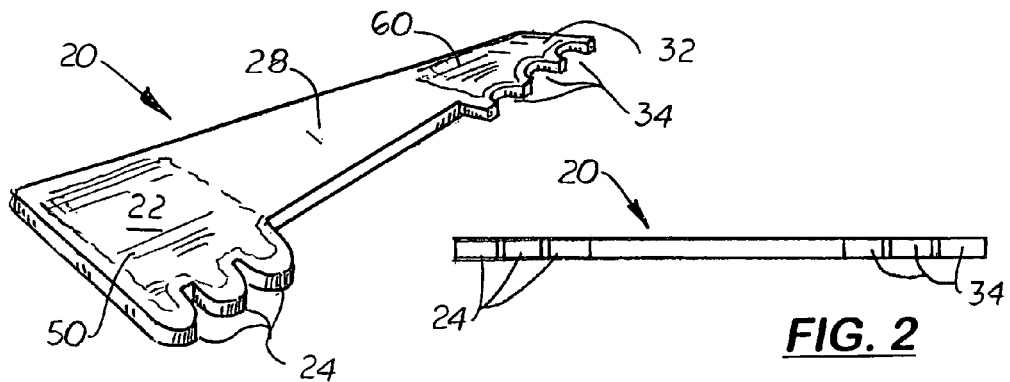
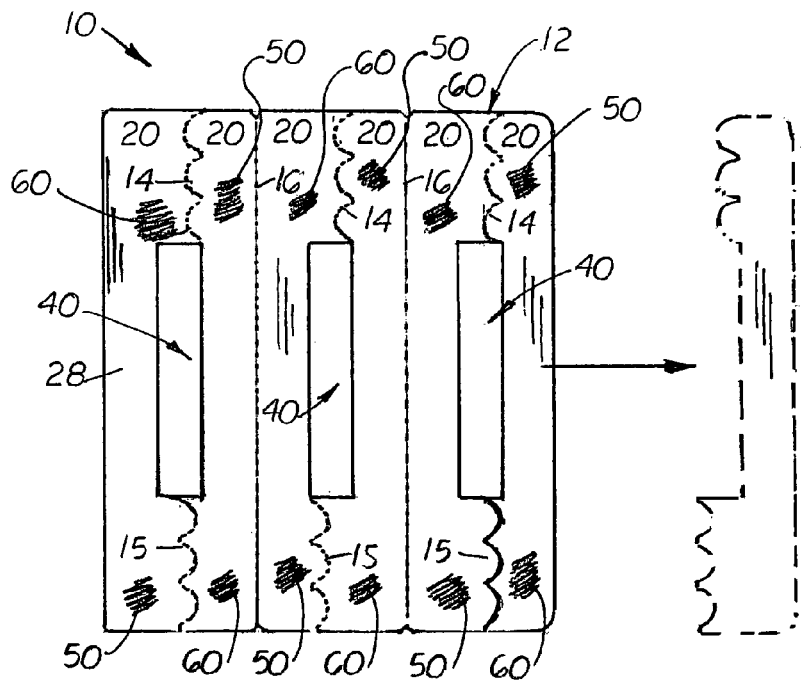

DISPOSABLE, BIODEGRADABLE, PORTABLE DENTAL IMPLEMENT

BACKGROUND OF THE INVENTION

1. Field of the Invention

This invention pertains to personal, oral hygiene products and more particularly to such products designed for portability in the user's purse or pocket and are disposable and biodegradable.

2. Description of the Related Art

Most dentist and dental hygienists recommend that their patients brush and floss between their teeth and message their gums at least twice a day. Unfortunately, many patients commute several hours each day and are away from their homes for long periods and do not carry a toothbrush, dental floss or a gum massager with them. Today, motor vehicle drivers and passengers often spend more and more time sitting in traffic and away from home or work. While public use of chewing gum and toothpicks are acceptable, brushing teeth and massaging gums with a standard toothbrush in public is generally not acceptable. If a person massaging gums with a standard toothbrush in public is generally not acceptable. If a person chooses to use a standard toothbrush while sitting in traffic, he or she must find a compact storage container for storing the saliva wetted toothbrush between uses.

SUMMARY OF THE INVENTION

It is an object of the present invention to provide a plurality of disposable dental implements that can be stored in a compact configuration.

It is another object of the present invention to provide a plurality of dental implements joined together to form a large planar structure that can be stored in a glove box, a purse, a coat pocket, a backpack or a suitcase that can be individually removed and used.

It is another object of the present invention to provide a disposable dental implement that includes a toothbrush end and a gum massaging end.

It is a further object of the present invention to provide such a dental implement that is made of disposable paper that is soaked with dried toothpaste that can be activated by saliva.

These and other objects are met by a multiple, disposable, biodegradable toothbrush dispensing system disclosed herein in which a plurality of disposable, flat toothbrushes are formed from a large, planar blank. Each toothbrush is a flat planar structure that includes a toothbrush head and a gum massager head that is formed on opposite ends of an elongated shank. The toothbrushes are created by perforation lines formed in the blank with adjacent toothbrushes aligned on the blank in an alternating, head-to-toe and toe-to-head manner. More specifically, the toothbrush head includes a plurality of concave ridges formed while the gum massaging head is made of a plurality of convex curved ridges complimentary in shape with the concave ridges on the adjacent toothbrush.

In the preferred embodiment, the planar blank is made of disposable paper and embedded with dry toothpaste or mouthwash which is activated by the user's saliva when used.

DESCRIPTION OF THE DRAWINGS

FIG. 1 is a perspective view of a single disposable toothbrush with a brushing head and a gum massaging head on opposite ends.

FIG. 2 is a front elevational view of the disposable toothbrush shown in FIG. 1.

FIG. 3 is a right side elevational view of the disposable toothbrush shown in FIGS. 1 and 2.

FIG. 4 is a top plan view of the planar blank with a plurality of disposable toothbrushes formed thereon and showing one disposable toothbrush being detached from the blank.

DESCRIPTION OF THE PREFERRED EMBODIMENT(S)

Referring to the FIGS. there is shown a multiple, disposable, biodegradable dental implement dispensing system 10 in which a plurality of disposable, flat dental implements 20 are formed from a large, planar blank 12. Each dental implement 20 is a flat planar structure that includes a toothbrush head 22 and gum massager head 32 formed on opposite ends of a thin, elongated shank 28. Adjacent implements 20 are created by perforation lines 14, 15, and 16 formed in the planar blank 12 with the individual implements 20 aligned transversely in an alternating head to toe and toe to head manner on the blank 12.

In the preferred embodiment, the toothbrush head 22 includes a plurality of concave ridges 24 formed while the gum massaging head 32 is made of a plurality of convex curved ridges 34 complimentary with the concave ridges 24 on the adjacent toothbrush 20. The elongated shank 28 has a width slightly smaller than the toothbrush 20 and the gum massaging head 32 thereby forming an elongated, rectangular opening 40 between adjacent implements 20. The opening 40 reduces weight and allows the user to more easily separate individual implements 20 from the blank 12.

In the preferred embodiment, the blank 12 is made of disposable paper and embedded with dry, water soluble toothpaste powder 50 or mouthwash powder 60 which is activated by the user's saliva when used.

In compliance with the statute, the invention described herein has been described in language more or less specific as to structural features. It should be understood however, that the invention is not limited to the specific features shown, since the means and construction shown, is comprised only of the preferred embodiments for putting the invention into effect. The invention is therefore claimed in any of its forms or modifications within the legitimate and valid scope of the amended claims, appropriately interpreted in accordance with the doctrine of equivalents.

I claim:

1. A compact multiple, disposable, biodegradable dental implement system to be carried in a user's pocket or purse, comprising: a planar blank with a plurality of disposable, flat dental implements formed therein that are individually removable from the planar blank prior to use by a user, each said dental implement includes a flat toothbrush head and a flat gum massager head located on opposite ends of a flat elongated shank, said dental implements being complimentary shaped and aligned on said planar blank with adjacent said dental implements being arranged in an alternating, head-to-toe and toe-to-head manner on said planar blank, said dental implements being attached to said planar blank by perforated lines that hold each said dental implement on said planar blank and enable each said dental implement to be individually removed from said planar blank prior to use, said planar blank being made of disposable paper and embedded with a dry oral powder which dissolves in saliva when said dental implement is removed from said planar blank and placed inside a user's mouth.

2. The disposable, biodegradable dental implement system, as recited in claim 1, wherein said dry oral powder is a toothpaste.

3. The disposable, biodegradable dental implement system, as recited in claim 1, wherein said dry oral powder is a mouth wash.

4. The disposable, biodegradable dental implement system, as recited in claim 1, wherein said toothbrush head includes a plurality of perpendicularly aligned concave ridges.

5. The disposable, biodegradable dental implement, system as recited in claim 1, wherein said gum massaging head includes a plurality of perpendicularly aligned convex curved ridges.

6. The disposable, biodegradable dental implement system, as recited in claim 4, wherein said gum massaging head includes a plurality of perpendicularly aligned convex curved ridges.

7. The disposable, biodegradable dental implement system, as recited in claim 6, wherein said concave ridges and said convex ridges are complimentary and shaped by perforated lines cut on said blank.

* * * * *